(12) United States Patent
Rao et al.

(10) Patent No.: US 8,426,590 B2
(45) Date of Patent: Apr. 23, 2013

(54) PROCESS FOR THE PREPARATION OF DOXAZOSIN AND SALTS THEREOF

(75) Inventors: Dharmaraj Ramachandra Rao, Maharashtra (IN); Rajendra Narayanrao Kankan, Maharashtra (IN); Dilip Ramdas Birari, Maharashtra (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 13/257,003

(22) PCT Filed: Mar. 23, 2010

(86) PCT No.: PCT/GB2010/000545
§ 371 (c)(1),
(2), (4) Date: Nov. 4, 2011

(87) PCT Pub. No.: WO2010/109185
PCT Pub. Date: Sep. 30, 2010

(65) Prior Publication Data
US 2012/0041199 A1    Feb. 16, 2012

(30) Foreign Application Priority Data

Mar. 23, 2009  (IN) .................. 667/MUM/2009

(51) Int. Cl.
*C07D 405/14*     (2006.01)
*C07D 405/06*     (2006.01)

(52) U.S. Cl.
USPC ....................... 544/291; 548/311.7

(58) Field of Classification Search ............... 544/291; 548/311.7
See application file for complete search history.

(56) References Cited

U.S. PATENT DOCUMENTS 4,188,390 A    2/1980  Campbell

FOREIGN PATENT DOCUMENTS

WO    2010109185  A2    9/2010
WO    2010109185  A3    9/2010

OTHER PUBLICATIONS

Campbell, Simon F., et al., 2,4-Diamino-6,7-dimethoxyquinazolines. 1. 2-[4[(1,4-Benzodioxan-2-ylcarbonyl)piperazin-1-yl] Derivatives as a1-Adrenoceptor Antagonists and Antihypertensive Agents, XP-002225055, J. Med. Chem., 1987, vol. 30, pp. 49-57, American Chemical Society.
Foreign communication from the priority application—International Search Report and Written Opinion, PCT/GB2010/000545, Mar. 11, 2011, 9 pages.
Foreign communication from the priority application—International Preliminary Report on Patentability, PCT/GB2010/000545, Sep. 27, 2011, 14 pages.
Kumaraswamy, G., et al., "A reliable multigram synthesis of (+/−) Doxazosin," Organic Preparations and Procedures Int., 2003, vol. 35, No. 6, pp. 603-608, Organic Preparations and Procedures Inc.

*Primary Examiner* — Kristin Bianchi
(74) *Attorney, Agent, or Firm* — Conley Rose, P.C.; Rodney B. Carroll

(57) ABSTRACT

The present invention relates to a process for the preparation of doxazosin or salts thereof.

24 Claims, No Drawings

US 8,426,590 B2

PROCESS FOR THE PREPARATION OF DOXAZOSIN AND SALTS THEREOF

CROSS-REFERENCE TO RELATED APPLICATIONS

This application is a filing under 35 U.S.C. 371 of International Application No. PCT/GB2010/000545 filed Mar. 23, 2010 entitled "Process for the Preparation of Doxazosin and Salts Thereof," claiming priority of Indian Patent Application No. 667/MUM/2009 filed Mar. 23, 2009, which applications are incorporated by reference herein in their entirety.

FIELD OF INVENTION

The present invention relates to a process for the preparation of doxazosin or salts thereof.

BACKGROUND OF THE INVENTION

Doxazosin is chemically known as 4-amino-2-[4-(1,4-benzodioxan-2-carbonyl)piperazin-1-yl]-6,7-dimethoxyquinazoline and is represented by formula I.

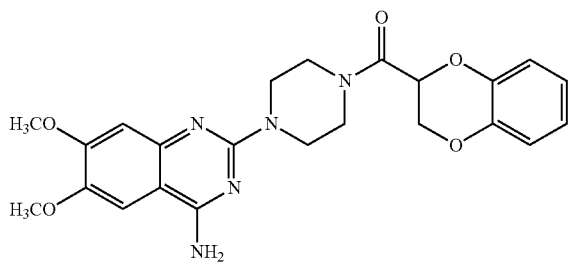

Formula I

Doxazosin, a quinazoline compound, is an alpha-1 adrenergic receptor blocker used to treat high blood pressure, benign prostatic hyperplasia and elevated serum low density lipoproteins. It inhibits the binding of norepinephrine to alpha receptors in the autonomic nervous system thus causing vasodilation, and a decrease in peripheral vascular resistance which further leads to decrease in blood pressure.

U.S. Pat. No. 4,188,390 discloses doxazosin, its pharmaceutically acceptable salts and process of preparation thereof. U.S. Pat. No. 4,188,390 covers the preparation of doxazosin hydrochloride only and not of the doxazosin base.

The doxazosin hydrochloride is prepared by reacting 4-amino-2-chloro-6,7-dimethoxy quinazoline with N-(1,4-benzodioxan-2-carbonyl)piperazine as represented in following reaction Scheme 1.

Scheme 1

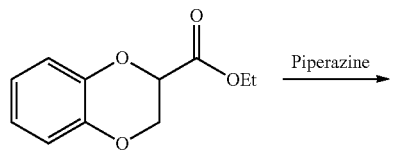

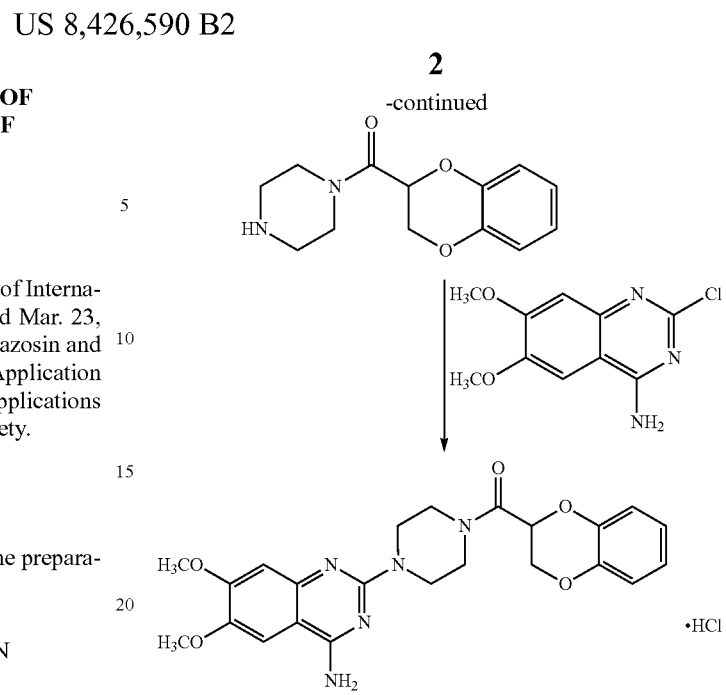

The major problem associated with the disclosed process is that reaction of piperazine with ethyl 2,3-dihydrobenzo[1,4] dioxin-2-carboxylate results in formation of the bis-amide impurity.

Organic Preparations and Procedures International (2003); 35; 603-608 describes the procedure for synthesizing doxazosin by treating (2,3-dihydrobenzo[b][1,4]dioxin-2-yl)(piperazin-1-yl)methanone with 2-chloro-6,7-dimethoxy quinazolin-4-amine in presence of n-butanol to obtain doxazosin hydrochloride; which on further treatment with aqueous ammonia solution yields doxazosin base.

However, the process described in Organic Preparations and Procedures International (2003) involves the use of highly toxic reagents like thionyl chloride which is not convenient to handle at industrial scale. Also, the use of the reagent in the process leads to generation of unwanted side product such as dimeric impurity, formula A, which in turn affects the overall yield of the final product. Hence, the preparation of doxazosin hydrochloride by this process is not feasible at plant scale.

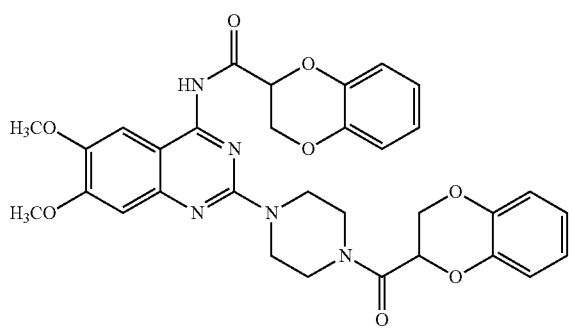

Formula A

Other patents disclose preparation of doxazosin mesylate and its polymorphs.

From the prior art it is clear that there has been no disclosure of a process of preparing doxazosin. The known processes give the preparation of doxazosin salt which on treatment with a base yields doxazosin. The inventors have therefore felt a need to develop a process for the preparation of doxazosin that is simple, easy to scale up and industrially acceptable.

OBJECT OF THE INVENTION

The main object of the present invention is to provide a process for the preparation of doxazosin base or its pharmaceutically acceptable salts.

Another object of the present invention is to provide an economical, eco-friendly and industrially acceptable process for the preparation of doxazosin.

SUMMARY OF THE INVENTION

According to first aspect of the present invention, there is provided a process for preparing doxazosin base of formula (I), which process comprises reacting 2,3-dihydro-benzo[1,4]dioxine-2-carboxylic acid derivative of formula (II) with 6,7-dimethoxy-2-(piperazin-1-yl)quinazolin-4-amine (III), as represented in below reaction Scheme 2.

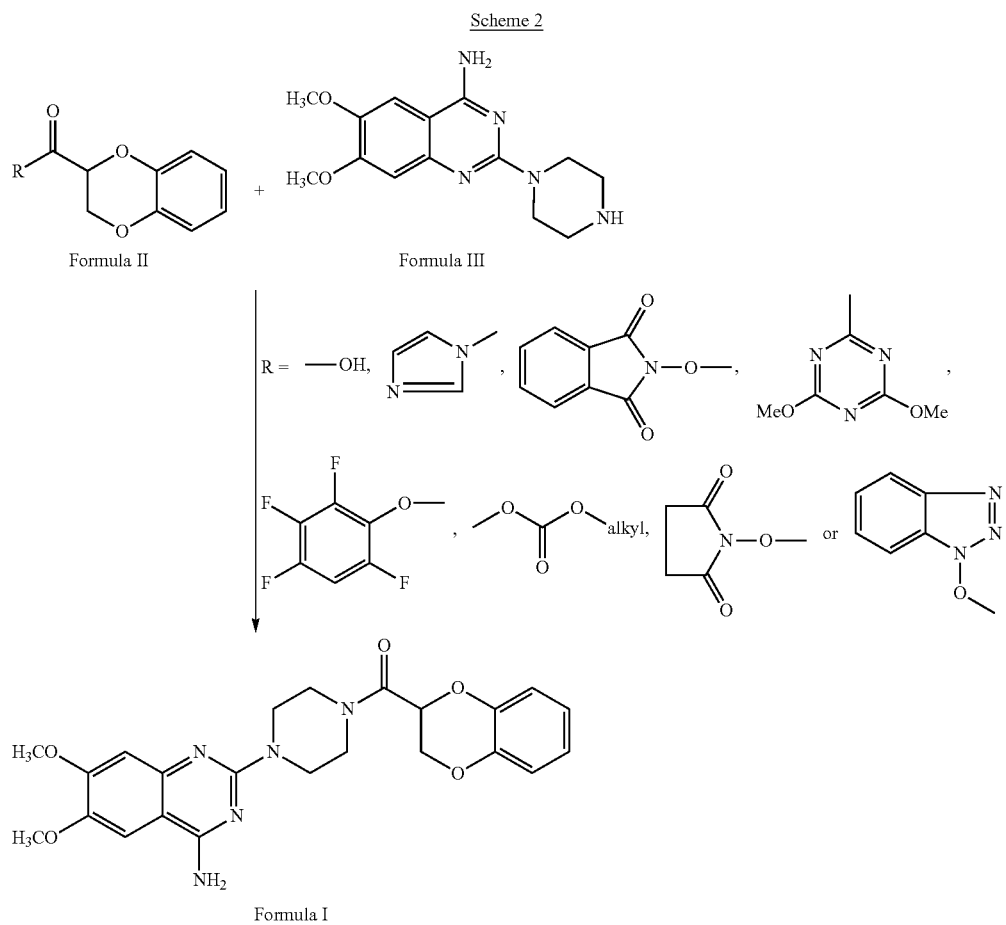

The doxazosin base of the process of present invention is prepared by carrying out the reaction in presence of suitable activating agent or coupling agent or mixtures thereof.

Accordingly, in an aspect of the invention, when R=OH, the condensation reaction is carried out in presence of coupling agent.

In an embodiment, when R=OH, the doxazosin is prepared by process which comprises condensing 2,3-dihydro-benzo[1,4]dioxine-2-carboxylic acid (IV) with 6,7-dimethoxy-2-(piperazin-1-yl)quinazolin-4-amine (III) in presence of coupling agent to form the doxazosin of formula (I). The doxazosin may optionally be converted to a salt thereof.

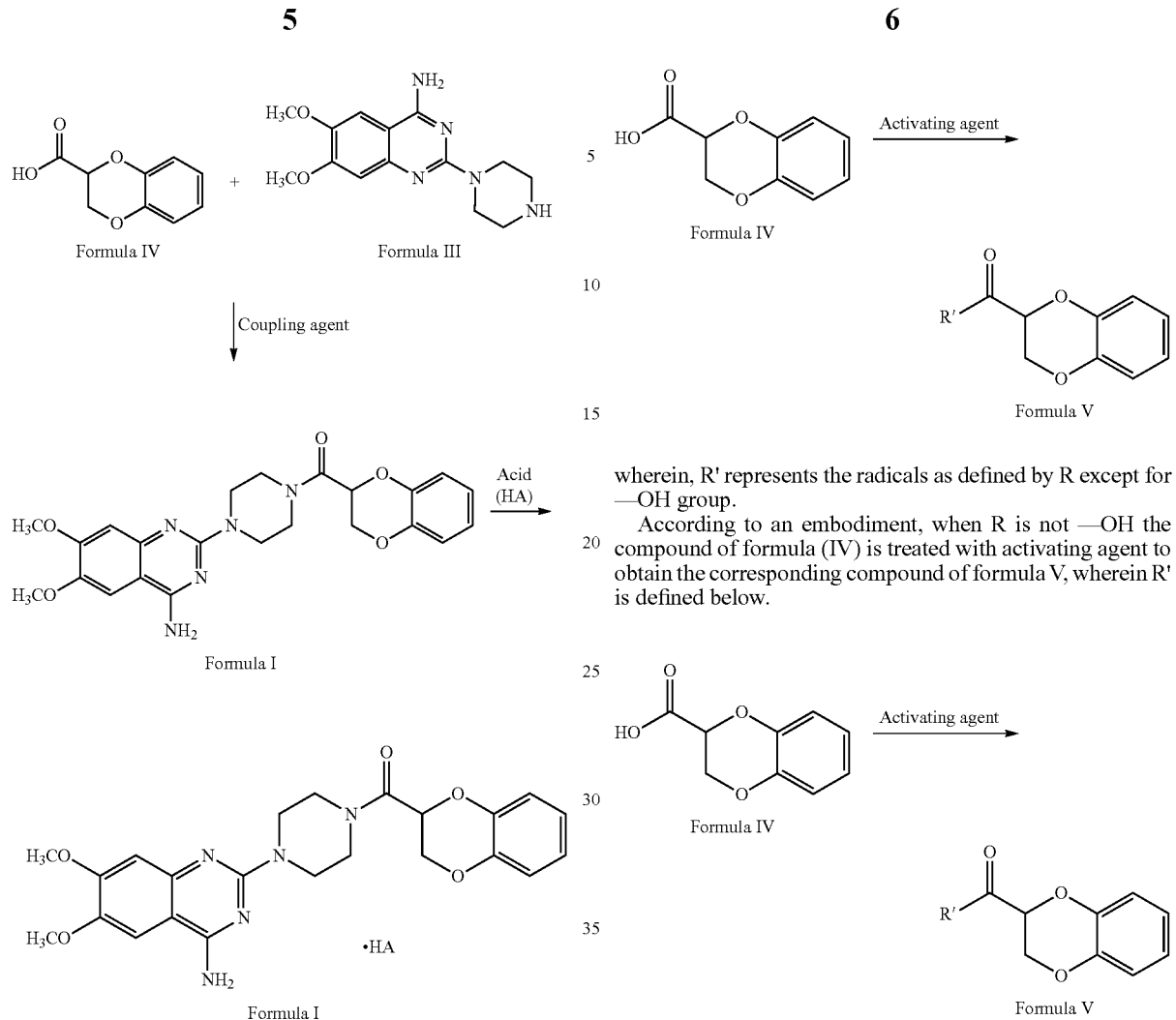

In an embodiment, the term "coupling agent" may be taken to mean a chemical substance capable of activating the free carboxyl group through the formation of highly reactive intermediate, that are subject to facile nucleophilic attack by amino functional groups leading to peptide link formation. In a further embodiment, the term "coupling agent" may be taken to mean a chemical substance that couples compounds of formula (IV) and formula (III) to form doxazosin of formula (I).

The coupling agent used for the reaction may be selected from groups such as carbodiimide, aminium or phosphonium salts. The coupling agents are selected from dicyclohexylcarbodiimide, diisopropylcarbodiimide, 1-ethyl-3-(3-dimethylaminopropyl) carbodiimide, hydroxy benzotriazole, [1,2,3]triazolo[4,5-b]pyridin-3-ol, O-(benzotriazol-1-yl)-N,N,N',N'-tetramethyluronium tetrafluoroborate, O-benzotriazole-N,N,N',N'-tetramethyl uraniumhexafluorophosphate, benzotriazole-1-yl-oxy-tris(dimethylamino)phosphonium hexafluorophosphate, (benzotriazol-1-yloxy)tripyrrolidinophosphonium hexafluorophosphate. Preferably the coupling agent used in the process of present invention is dicyclohexylcarbodiimide.

According to another embodiment, when R is not —OH the compound of formula (IV) is treated with activating agent to obtain the corresponding compound of formula V:

wherein, R' represents the radicals as defined by R except for —OH group.

According to an embodiment, when R is not —OH the compound of formula (IV) is treated with activating agent to obtain the corresponding compound of formula V, wherein R' is defined below.

wherein R'=

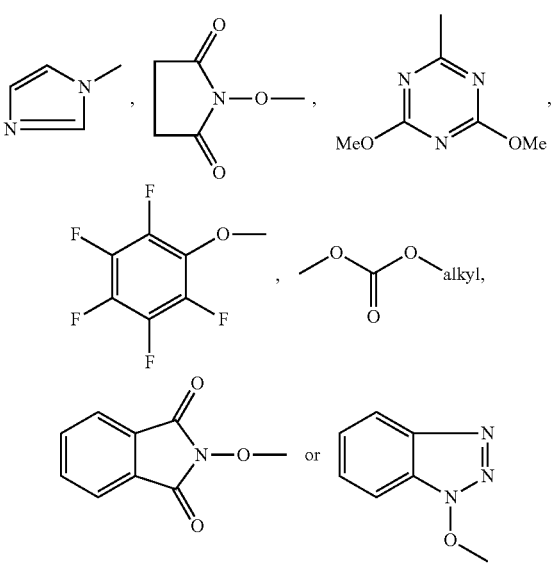

According to another aspect there is provided a process for preparing doxazosin which comprises:

(a) condensing 2,3-dihydro-benzo[1,4]dioxine-2-carboxylic acid (IV) with an activating agent to obtain corresponding intermediate compound of formula (V); and (b) reacting intermediate compound of formula (V) with 6,7-dimethoxy-2-(piperazin-1-yl) quinazolin-4-amine (III) to obtain doxazosin (I). The doxazosin may optionally be converted to a salt thereof.

The solvent used in the process for the preparation of doxazosin base (I) is selected from acetonitrile, dioxane, tetrahydrofuran, ethyl acetate or dichloromethane. Preferably, the solvent used is tetrahydrofuran.

In an aspect, the doxazosin obtained from the above processes is isolated from the reaction mixture by replacing the solvent with another solvent.

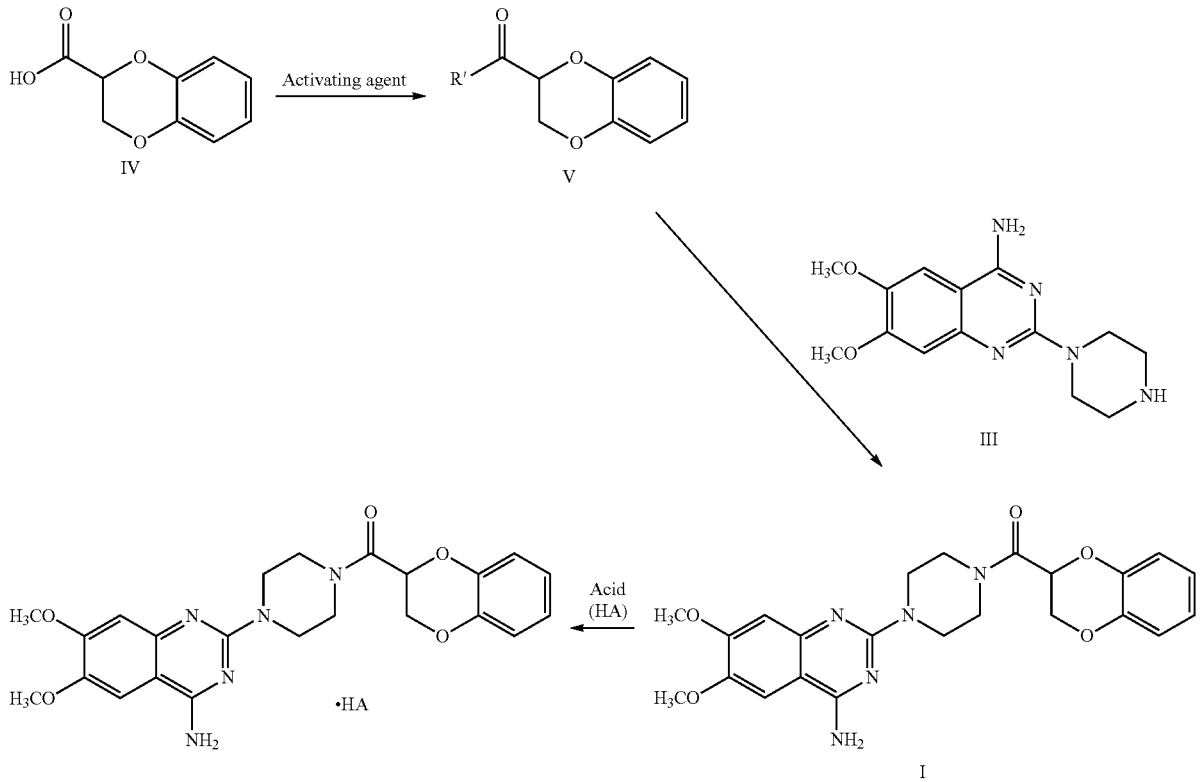

In an embodiment, the term "activating agent" may be taken to mean an agent that activates functional group for substitution or elimination reaction. In a further embodiment, the term "activating agent" may be taken to mean an agent that activates the compound of formula (IV) to form compound of formula (V).

The activating agent used for the preparation of doxazosin base may be selected from N,N'-carbonyldiimidazole, hydroxybenzotriazole, N-hydroxysuccinimide, N-hydroxy phthalimide, pentafluorophenol, 2-chloro-4,6-dimethoxy-1,3,5-triazine or alkyl chloro formates.

In a preferred embodiment, R is imidazole ring and the compound of formula (V) has the formula (VA).

VA

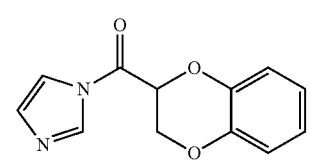

Suitably, the reaction is carried out without isolation of intermediate compound of formula (V). In other words, the intermediate is not isolated from the reaction mixture.

In an embodiment, the second solvent used is selected from acetonitrile, acetone, dimethyl formamide or dichloromethane; preferably the solvent is acetone.

The use of coupling or activating agent in the process of present invention minimizes the dimeric impurity of formula (A) up to 0.01%.

In another embodiment, the solvent used for preparing doxazosin salt is a polar aprotic solvent.

According to yet another aspect of the present invention, there is provided (2,3-dihydrobenzo[b][1,4]dioxin-2-yl)(1H-imidazol-1-yl)methanone of formula (VA).

According to still another aspect of the present invention, there is provided doxazosin base prepared according to a process described above.

According to another aspect of the present invention, there is provided doxazosin salt prepared according to a process described above.

According to a further aspect of the present invention, there is provided a pharmaceutical composition comprising doxazosin or salts thereof, prepared according to a process described above, together with one or more excipients.

According to another aspect of the present invention, there is provided doxazosin or salts thereof prepared according to process described above for use in the treatment of atherosclerosis.

DETAILED DESCRIPTION OF THE INVENTION

The invention will now be described in detail in connection with certain preferred and optional embodiments, so that various aspects thereof may be more fully understood and appreciated.

The present invention provides a simple, economical and easy scale-up process for the synthesis of doxazosin in good yield and high purity.

In an embodiment of the present invention, there is provided a process for synthesis of doxazosin (I) as depicted below in reaction Scheme 2,

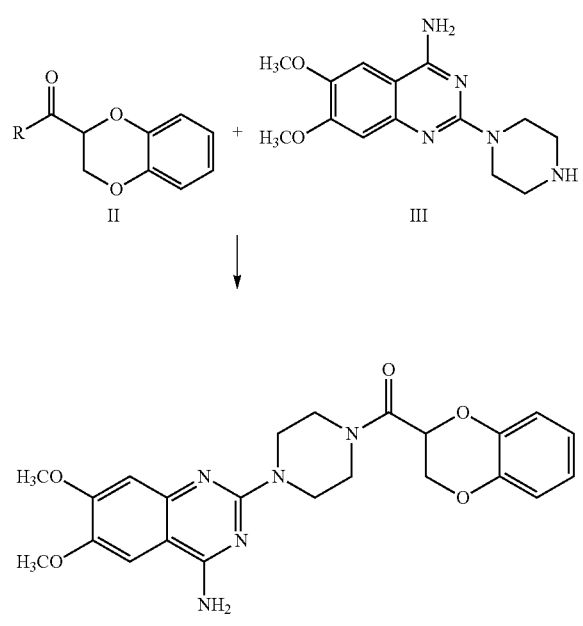

wherein,

R=

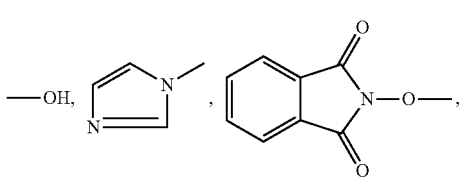

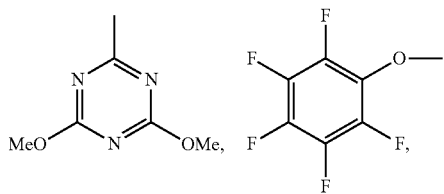

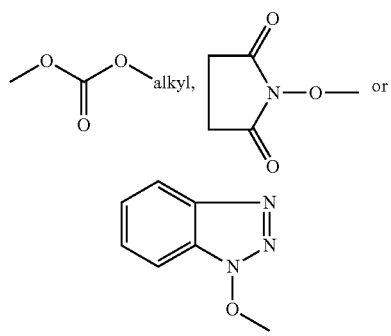

Accordingly, in an embodiment, when R=OH, the condensation reaction is carried out in presence of coupling agent.

In an embodiment, when R=OH, the process of preparation of doxazosin (I) or salt thereof, comprises:
(a) reacting 2,3-dihydro-benzo[1,4]dioxine-2-carboxylic acid (IV)

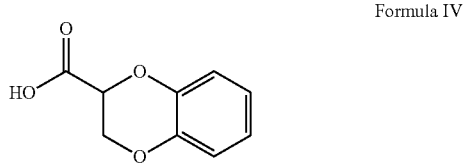 [SMILES: O=C(O)C1COc2ccccc2O1]

Formula IV with 6,7-dimethoxy-2-(piperazin-1-yl)quinazolin-4-amine (III)

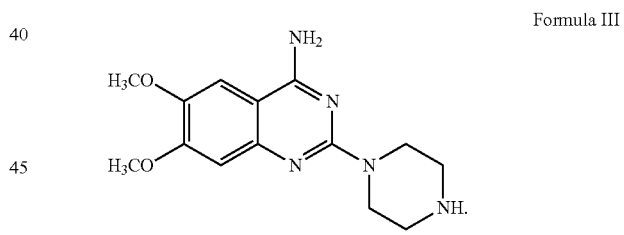

Formula III in presence of a coupling agent.

The coupling agent used for the preparation of doxazosin base may be selected from groups such as carbodiimide, aminium or phosphonium salts. The coupling agents are selected from dicyclohexylcarbodiimide, diisopropylcarbodiimide, 1-ethyl-3-(3-dimethylaminopropyl)carbodiimide, hydroxy benzotriazole, [1,2,3]triazolo[4,5-b]pyridin-3-ol, O-(benzotriazol-1-yl)-N,N,N',N'-tetramethyluronium tetrafluoroborate, O-benzotriazole-N,N,N',N'-tetramethyluroniumhexafluorophosphate, benzotriazole-1-yl-oxy-tris(dimethyl amino)phosphonium hexafluorophosphate, (benzotriazol-1-yloxy)tripyrrolidino phosphonium hexafluorophosphate.

In preferred embodiment, the coupling agent used in the process of present invention is dicyclohexylcarbodiimide.

In another embodiment, when R is not OH, compound of formula (IV) is treated with an activating agent to give corresponding intermediate of formula (V).

According to another aspect, the process of preparation of doxazosin (I), comprises (a) condensing 2,3-dihydro-1,4-benzodioxine-2-carboxylic acid (IV),

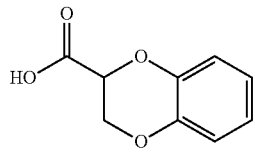

Formula IV with activating agent to obtain 2,3-dihydro-1,4-benzodioxine derivative of formula (V);

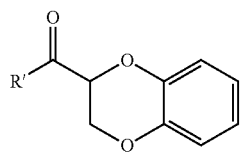

Formula V (b) reacting compound of formula (V) with 6,7-dimethoxy-2-(piperazin-1-yl) quinazolin-4-amine (III)

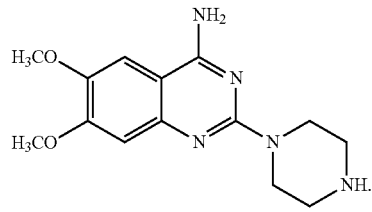

Formula III to obtain doxazosin of formula (I). The doxazosin may optionally be converted to a salt thereof.

The acid used for the preparation of doxazosin salt may be inorganic, like hydrochloric acid, or organic, like methanesulphonic acid.

The activating agent used for the process of present invention is selected from N,N'-carbonyldiimidazole, hydroxybenzotriazole, N-hydroxysuccinimide, N-hydroxy phthalimide, pentafluorophenol, 2-chloro-4,6-dimethoxy-1,3,5-triazine or alkyl chloro formates.

In a preferred embodiment, the activating agent used is N,N'-carbonyldiimidazole.

In a further embodiment, when the activating agent is N,N'-carbonyldiimidazole the compound of formula V has the formula:

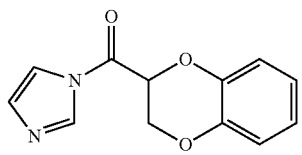

Formula VA

Suitably, the reaction is carried out without isolation of intermediate compound of formula (V). In other words, the intermediate is not isolated from the reaction mixture.

In an embodiment, the process is a one-pot process. In other words, the steps resulting to the preparation of doxazosin (I) of the present invention are carried out in a single reaction vessel.

In another embodiment, the solvent used in the process for the preparation of doxazosin of formula (I) is selected from acetonitrile, dioxane, tetrahydrofuran, ethyl acetate or dichloromethane. Preferably, the solvent used is tetrahydrofuran.

The process of present invention is preferably carried out at a temperature below 40° C.

In an embodiment, the doxazosin obtained from the above processes is isolated from the reaction mixture by replacing the solvent with another solvent.

In an embodiment, the second solvent is a polar aprotic solvent selected from acetonitrile, acetone, dimethyl formamide or dichloromethane. Preferably, doxazosin is isolated from reaction mixture by using acetone solvent.

The doxazosin of the present invention may optionally be recrystallised by suspending doxazosin in a polar solvent such as C1-C4 alcohol, such as methanol, and heating the mixture to reflux. The resulting suspension is cooled, filtered and dried at 50-65° C.

The use of coupling or activating agent in the process of present invention minimizes the dimeric impurity of formula (A) up to 0.01%.

The doxazosin salt of the present invention is prepared by dissolving doxazosin base (I) in a polar aprotic solvent which is selected from acetonitrile, acetone or dichloromethane. Preferably, doxazosin (I) is dissolved in acetone.

The doxazosin salt of the process of present invention is purified using polar solvent like methanol, ethanol, n-butanol or isopropanol, mainly methanol.

In an embodiment, the process of present invention eliminates the wastage of product, reduces the use cost associated with multiple reactors, reduces cleanup thus making the process more industrially viable.

In most preferred embodiment, the process of the present invention is depicted below in Scheme 3.

Scheme 3

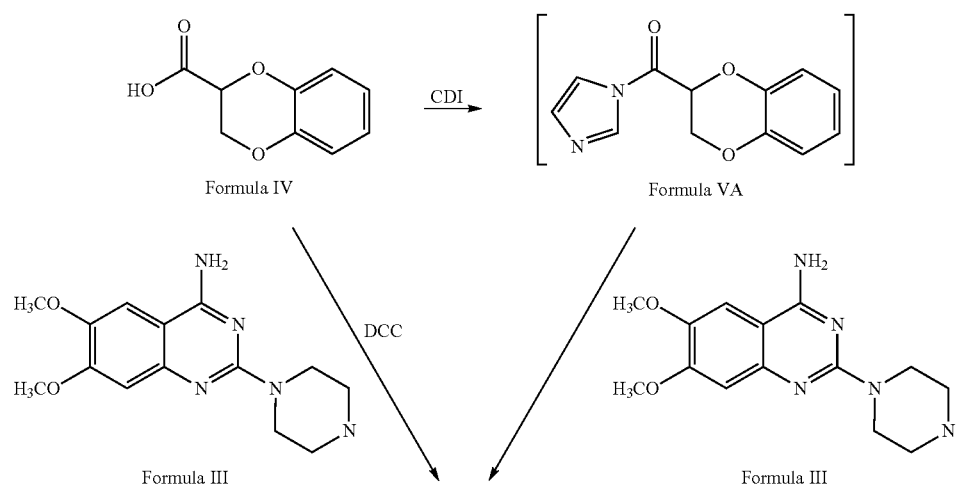

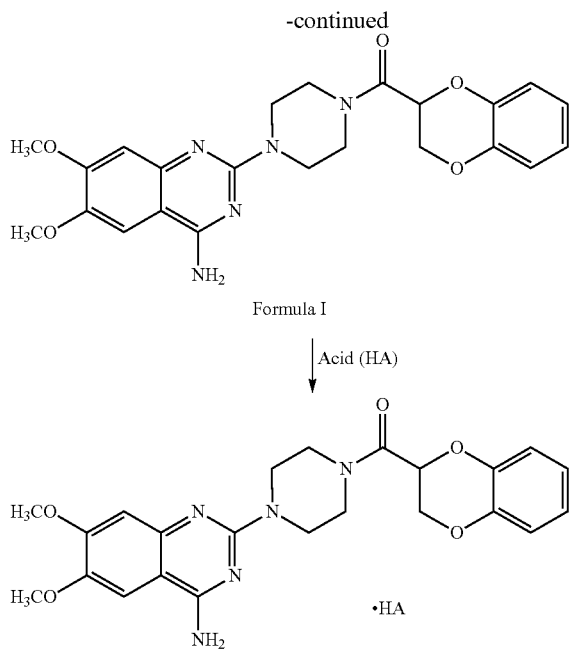

Formula I

↓ Acid (HA)

In a further aspect, the present invention provides a pharmaceutical composition comprising doxazosin or salts thereof prepared according to a process described above together with one or more excipients.

The invention also relates to the use of doxazosin or its salts prepared according to the process described above for the treatment of atherosclerosis.

EXAMPLES

The following examples, which include preferred embodiments, will serve to illustrate the practice of this invention, it being understood that the particulars shown are by way of example and for purpose of illustrative discussion of preferred embodiments of the invention. It will be appreciated that the invention may be modified within the scope of the appended claims.

Example 1

2,3-dihydro-1,4-benzodioxine-2-carboxylic acid (0.38 mol; 68.51 g) and tetrahydrofuran (500 ml) were charged and contents were stirred at 20-25° C. for 5-10 min to get a clear solution. N,N-carbonyl diimidazole (0.407 mol; 66.28 g) along with tetrahydrofuran (500 ml) was added to the solution and stirring continued at 20-25° C. for 2 hr to obtain solution A. In another round bottom flask, 6,7-dimethoxy-2-(piperazin-1-yl)quinazolin-4-amine (0.346 mol; 100 g) and tetrahydrofuran (1000 ml) were charged and stirred at 26-28° C. for 5-10 min to obtain a slurry. Solution A was added dropwise within 2-2.5 hr at 25-28° C. to the slurry. The reaction was monitored by HPLC. To the resulting clear reaction mass charcoal was added and contents were stirred at 26-28° C. for 45 min. The contents were filtered through celite and washed with tetrahydrofuran. The solvent was distilled out at 35° C. under reduced pressure to obtain solid residue. Acetone (1000 ml) was added to the solid and contents were refluxed for 2 hr. On cooling to 25-28° C., the slurry was filtered, washed with acetone and dried at 60° C. under reduced pressure to obtain 110 g of doxazosin base (HPLC purity –99.4%).

Example 2

Step A—0.0172 mol (3.096 g) of 2,3-dihydro-1,4-benzodioxine-2-carboxylic acid and 25 ml of tetrahydrofuran were charged in a round bottom flask. The reaction mixture was stirred at 20-25° C. for 5-10 min. To the clear solution N,N-carbonyl diimidazole (0.018 mol; 2.92 g) and 25 ml of tetrahydrofuran was added and stirred at 20-25° C. for 2 hr. The solution was concentrated to obtain 1-(2,3-dihydro-1,4-benzodioxin-2-ylcarbonyl)-1H-imidazole.

Step B—In another round bottom flask, 6,7-dimethoxy-2-(piperazin-1-yl)quinazolin-4-amine (0.017 mol; 4.913 g) and tetrahydrofuran (50 ml) were added and stirred at 26-28° C. for 5-10 min. To this slurry solution of 1-(2,3-dihydro-1,4-benzodioxin-2-ylcarbonyl)-1H-imidazole in tetrahydrofuran was added dropwise within 2-2.5 hr at room temperature. The resulting clear reaction mass was charcoalized and stirred at 26-28° C. for 45 min. The slurry was filtered through celite and washed with tetrahydrofuran. The solvent was distilled out at 35° C. under reduced pressure and solid was obtained. Acetone (1000 ml) was added to the solid and refluxed for 2 hr. On cooling to room temperature, the slurry was filtered, washed with acetone and dried at 60° C. under reduced pressure to obtain solid.

Step C—To the solid, obtained from step B, methanol (52 ml) was added and contents heated to reflux for 1 hr. The slurry was cooled to room temperature, filtered, washed with methanol and dried at 60° C. under reduced pressure to obtain 5.5 g of pure doxazosin base (HPLC purity –99.26%).

Example 3

In a reaction vessel, 0.25 mol (45.0 g) of 2,3-dihydro-1,4-benzodioxine-2-carboxylic acid, tetrahydrofuran (328 ml) and 6,7-dimethoxy-2-(piperazin-1-yl)quinazolin-4-amine (0.22 mol; 63.58 g) were charged and contents were stirred at 20-25° C. for 5-10 min. To the resulting mixture dicyclohexylcarbodiimide (0.26 mol; 54.0 g) was added and stirring continued at 20-25° C. for 1.5 hr. To the resulting reaction mass charcoal was added and contents were stirred at 26-28° C. for 45 min. The contents were filtered through celite and washed with tetrahydrofuran. The solvent was distilled out at 35° C. under reduced pressure to obtain solid residue. Acetone (1000 ml) was added to the solid and contents were refluxed for 2 hr. On cooling to 25-28° C., the slurry was filtered, washed with acetone and dried at 60° C. under reduced pressure to obtain 93 g of doxazosin base (HPLC purity –99.0%).

Example 4

Doxazosin base (0.277 mol; 125 g) was charged in acetone (1875 ml) and stirred at 25° C. to obtain slurry. On cooling the slurry to 10-15° C., methanesulphonic acid (0.33 mol; 31.96 g) was added to it. The contents were stirred for 10-15 min at 10-15° C. and then stirring continued at 25° C. for 2 hr. The solid obtained was filtered, washed with acetone and dried at 50-55° C. to obtain solid. The solid was purified by refluxing in methanol (1500 ml) for 1 hr. The slurry was cooled to room temperature, filtered, washed with methanol and then dried at 60° C. under reduced pressure to obtain 135 g of pure doxazosin mesylate (HPLC purity –99.81%).

Example 5

Doxazosin base (0.110 mol; 49.61 g) was charged in acetone (750 ml) and stirred at 25° C. to obtain slurry. On cooling the slurry to 10-15° C., hydrochloric acid solution was added till the pH was 2-3. The contents were stirred for 10-15 min at 10-15° C. and then stirring continued at 25° C. for 2 hr. The solid obtained was filtered, washed with acetone and dried at 50-55° C. to obtain solid product. The solid was purified by refluxing with methanol (600 ml) for 1 hr. The slurry was cooled to room temperature, filtered, washed with methanol and then dried at 60° C. under reduced pressure to obtain 51 g of pure doxazosin hydrochloride (HPLC purity –99.77%).

The invention claimed is:
1. A process for preparing doxazosin of the formula (I)

Formula I

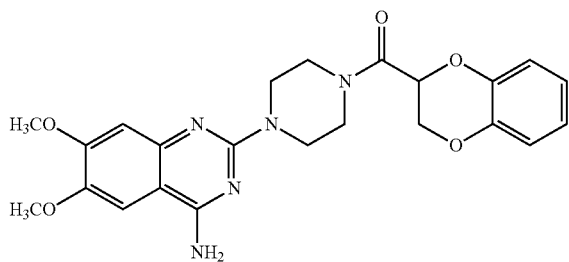

comprising condensing compound of formula (II),

Formula II

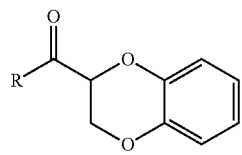

wherein,
R=

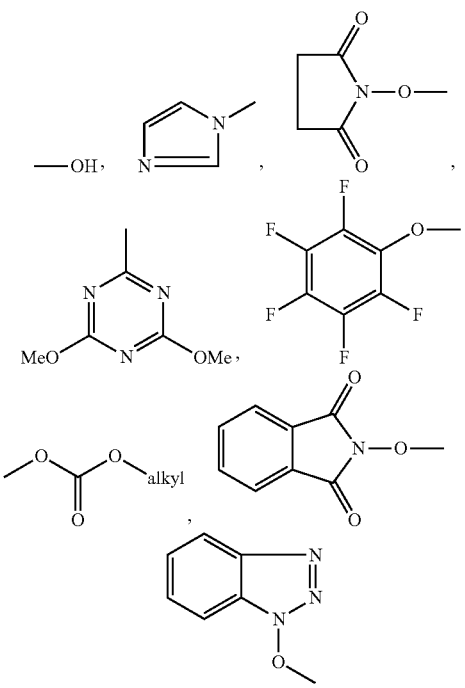

with 6,7-dimethoxy-2-(piperazin-1-yl)quinazolin-4-amine of formula (III)

Formula III

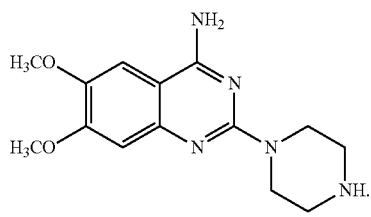

2. The process for preparing doxazosin according to claim 1, wherein when R=OH, condensation is carried out in presence of coupling agent.
3. The process for preparing doxazosin according to claim 2, wherein the coupling agent is selected from carbodiimide, aminium or phosphonium salts.
4. The process for preparing doxazosin according to claim 2, wherein the coupling agent is selected from dicyclohexylcarbodiimide, diisopropylcarbodiimide, 1-ethyl-3-(3-dimethylaminopropyl) carbodiimide, hydroxy benzotriazole, [1,2,3]triazolo[4,5-b]pyridin-3-ol, O-(benzotriazol-1-yl)-N,N,N',N'-tetramethyl uronium tetrafluoroborate, O-benzotriazole-N,N,N',N'-tetramethyluronium hexafluorophosphate, benzotriazole-1-yl-oxy-tris (dimethyl amino)phosphonium hexafluorophosphate or (benzotriazol-1-yloxy)tripyrrolidinophosphonium hexafluorophosphate.
5. The process for preparing doxazosin according to claim 2, wherein the coupling agent is dicyclohexylcarbodiimide.
6. The process for preparing doxazosin according to claim 1, wherein when R is not —OH,
i) compound of formula (IV) is reacted with an activating agent to obtain the corresponding intermediate (V)

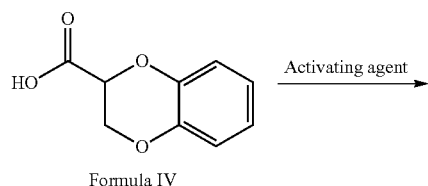

Formula IV

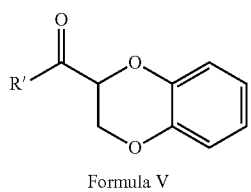

Formula V wherein, R' represents the radicals as defined by R except for —OH group ; and ii) compound of formula (V) is condensed with 6,7-dimethoxy-2-(piperazin-1-yl)quinazolin-4-amine of formula (III)

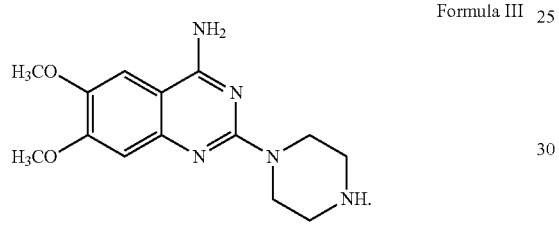

Formula III

7. The process for preparing doxazosin according to claim 6, wherein the activating agent used is selected from N,N'-carbonyldiimidazole, hydroxybenzotriazole, N-hydroxysuccinimide, N-hydroxy phthalimide, pentafluorophenol, 2-chloro-4,6-dimethoxy-1,3,5-triazine or alkyl chloro formates.

8. The process for preparing doxazosin according to claim 6, wherein the activating agent used is N,N'-carbonyldiimidazole.

9. The process according to claim 6, wherein the intermediate of formula (V) is not isolated before it is reacted with the compound of formula (III).

10. A process for preparing doxazosin salt, comprising dissolving the doxazosin base according to claim 1 in a solvent and then treating with an acid.

11. The process according to claim 10, wherein the solvent is selected from acetonitrile, acetone, dichloromethane or a mixture thereof.

12. The process according to claim 10, wherein the acid used is hydrochloric acid or methanesulphonic acid.

13. A process for preparing doxazosin comprising:
(a) condensing 2,3-dihydro-benzo[1,4]dioxine-2-carboxylic acid of formula (IV),

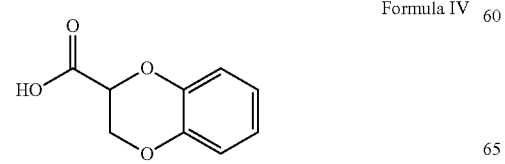

Formula IV with 6,7-dimethoxy-2-(piperazin-1-yl) quinazolin-4-amine of formula (III)

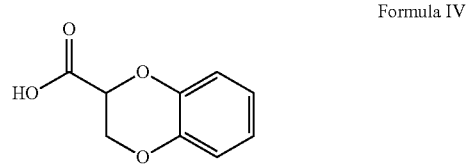 [SMILES: O=C(O)C1COc2ccccc2O1]

Formula III in presence of dicyclohexylcarbodiimide to obtain doxazosin; and
(b) optionally converting doxazosin to a salt thereof.

14. A process for preparing doxazosin comprising:
(a) condensing 2,3-dihydro-benzo[1,4]dioxine-2-carboxylic acid of formula (IV),

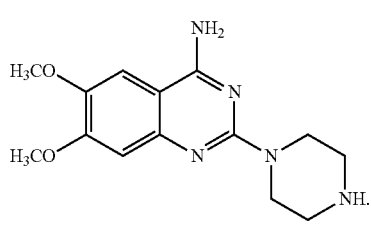

Formula IV with N,N'-carbonyldiimidazole to obtain (2,3-dihydro-benzo[1,4]dioxin-2-yl)-imidazol-1-yl-methanone of formula (VA);

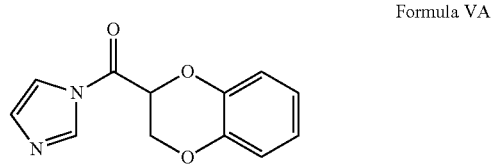 [SMILES: O=C(C1COc2ccccc2O1)n1ccnc1]

Formula VA (b) reacting compound of formula (VA) with 6,7-dimethoxy-2-(piperazin-1-yl) quinazolin-4-amine of formula (III)

Formula III to obtain doxazosin of formula (I); and

Formula I

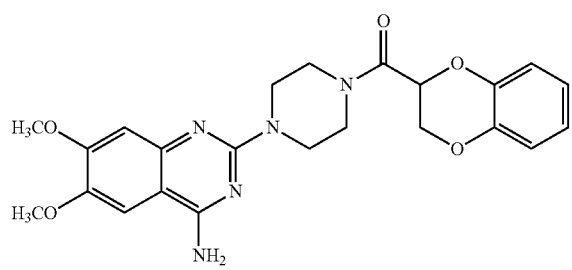

(c) optionally converting doxazosin to a salt thereof.

15. The process according to claim 13, when the doxazosin is converted to a salt thereof, the doxazosin salt is an acid addition salt.

16. The process according to claim 15, wherein the acid addition salt is hydrochloric acid or methanesulphonic acid.

17. The process according to claim 6, wherein the process is a one-pot process.

18. The process according to claim 14, wherein the (2,3-dihydro-benzo[1,4]dioxin-2-yl)-imidazol-1-yl-methanone of formula (VA) is not isolated before reacting with 6,7-dimethoxy-2-(piperazin-1-yl) quinazolin-4-amine of formula (III).

19. A process according to claim 1, wherein the condensation reaction is carried out in the presence of a solvent selected from acetonitrile, dioxane, tetrahydrofuran, ethyl acetate, dichloromethane or a mixture thereof.

20. The process according to claim 19, wherein the solvent used is tetrahydrofuran.

21. The process according to claim 19, further comprising isolating doxazosin by replacing the solvent with a second solvent.

22. The process according to claim 21, wherein the second solvent is a polar aprotic solvent.

23. The process according to claim 21, wherein the second solvent is selected from acetonitrile, acetone, dimethyl formamide, dichloromethane or a mixture thereof.

24. (2,3-dihydro-benzo[1,4]dioxin-2-yl)-imidazol-1-yl-methanone of formula (VA)

Formula VA

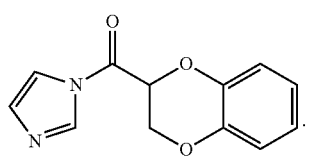

* * * * *